(12) United States Patent
Yen et al.

(10) Patent No.: US 8,907,062 B2
(45) Date of Patent: Dec. 9, 2014

(54) METHOD OF PRODUCING AND PURIFYING SOLUBLE RECOMBINANT COQ5 PROTEIN AND SOLUBLE RECOMBINANT COQ5 PROTEIN THEREOF

(75) Inventors: Hsiu-Chuan Yen, Tao-Yuan (TW); Shih-Wei Chen, Taipei (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 13/600,963

(22) Filed: Aug. 31, 2012

(65) Prior Publication Data

US 2013/0225792 A1  Aug. 29, 2013

(30) Foreign Application Priority Data

Feb. 24, 2012 (TW) ............................. 101106408 A (51) Int. Cl.
*C07K 14/00* (2006.01)

(52) U.S. Cl.
USPC ........................................ 530/350; 435/69.1

(58) Field of Classification Search
None
See application file for complete search history.

(56) References Cited

PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Measuring and increasing protein solubility. Trevino SR, Scholtz JM, Pace CN. J Pharm Sci. Oct. 2008;97(10):4155-66. doi: 10.1002/jps.21327.*
Bork (Genome Research, 2000,10:398-400).*
Chen (Powerpoint presentation given Sep. 2, 2011 at Chang Gung University, Taoyuan, Taiwan).*
The QIAexpressionist, A Handbook for High-Level Expression and Purification of 6XHis-Tagged Proteins, Jun. 2003.
Suzie W. Baba, Grigory I. Belogrudov, Justine C. Lee, Peter T. Lee, Jeff Strahan, Jennifer N. Shepherd, Catherine F. Clarke; Yeast Coq5 C-Methyltransferase Is Required for Stability of Other Polypeptides Involved in Coenzyme Q Biosynthesis; The Journal of Biological Chemistry, vol. 279, No. 11, Mar. 12, 2004, pp. 10052-10059.

* cited by examiner

Primary Examiner — Brian J Gangle
Assistant Examiner — Andrea McCollum
(74) Attorney, Agent, or Firm — Rosenberg, Klein & Lee (57) ABSTRACT

The present invention relates to a producing and purifying method of soluble recombinant coenzyme Q5 homolog (COQ5) protein, which is expressed in soluble form by *Escherichia coli* (*E. coli*), under native conditions. The method is characterized by pre-treating bacterial lysate with low concentration of ionic detergent, such as sodium dodecyl sulfate (SDS), before purification; and the purifying method is performed under native condition without using urea to avoid the problems of requiring lengthy processes to remove urea in purified protein solution or re-aggregation and precipitation of protein after removal of urea.

7 Claims, 5 Drawing Sheets

METHOD OF PRODUCING AND PURIFYING SOLUBLE RECOMBINANT COQ5 PROTEIN AND SOLUBLE RECOMBINANT COQ5 PROTEIN THEREOF

FIELD OF THE INVENTION

The present invention relates to a producing and purifying method of recombinant coenzyme Q5 homolog (COQ5) protein expressed in soluble form by *Escherichia coli* (*E. coli*). The purifying method is characterized by pre-treating bacterial lysate with low concentration of ionic detergent before purification; and performed in non-denaturing conditions to avoid the problems of urea removal from purified protein solution if purified under denaturing condition and of re-aggregation or precipitation of the purified protein upon removal of urea or during storage.

BACKGROUND OF THE INVENTION

Many human recombinant proteins form inclusion body or non-native form when expressed in *E. coli* and so denaturing conditions, such as the use of 8 M urea, have to be used to purify protein, which may cause trouble during protein purification and preparation of purified protein before antibody production than protein purified as soluble protein or under native conditions. For example, the procedures to purify proteins in inclusion body are more complicated than that for purifying soluble proteins. Moreover, if denaturing conditions are used to purify proteins, removal of urea in purified protein before antibody production is very troublesome, such as the use of lengthy buffer-exchange processes with concentrators, or even sodium dodecyl sulfate-polyacrylamide gel electrophoresis (SDS-PAGE) purification. Furthermore, very often proteins purified under denaturing conditions may become aggregated or form precipitation once the denaturing agent is removed and the protein is concentrated, which cause problems by reducing amount of protein yield available for antibody production and subsequent affinity purification of antibody. Attempts to refold such purified protein back to native form often do not work well or are difficult. On the other hand, only soluble recombinant protein, but not aggregated protein, can be used for pharmaceutical purposes and to study the biochemical properties, biological functions, and crystal structure.

Although antibodies generated against non-native form of protein or synthetic peptide for specific epitopes can be used for the purpose of Western blot analysis, the use of native protein as the antigen might produce more useful polyclonal antibody against dominant epitopes presented by natively folded protein. Moreover, antibody that can recognize epitopes the bided structure of mature protein would be needed for immunoprecipitation assay. Multiple try-and-error may be needed when only aiming at specific epitopes by synthetic peptides. Moreover, denatured recombinant proteins are often in aggregated or precipitated form, which cause low yield and high cost if using soluble fraction to immunize rabbits and is not suitable for further purification of antibody by affinity column.

Although administration of exogenous coenzyme $Q_{10}$ has been extensively used, the biosynthesis for endogenous coenzyme $Q_{10}$ and mechanisms for coenzyme $Q_{10}$ deficiency diseases in humans are poorly studied. The lack of validated commercial antibodies and soluble purified recombinant proteins for human PDSS and COQ proteins essential for terminal biosynthetic reactions of coenzyme $Q_{10}$ has been an obstacle in this area. COQ5 protein has been found to be essential as one of the nine COQ proteins essential for coenzyme $Q_6$ biosynthesis in yeast, but its role in humans for biosynthesis of coenzyme $Q_{10}$ has not been studied. Yeast COQ5 protein is a methyltransferase and a mitochondrial matrix protein associated with inner membrane that can form a multi-subunit complex with other COQ proteins in yeast (Baba et al., J Biol Chem 279: 10052, 2004). However, there has been no study on human COQ5 protein.

For making polyclonal antibody against nuclear DNA-encoded mitochondrial matrix protein by using recombinant protein as the antigen, most people just expressed full-length protein in *E. coli*. However, that should result in misfolded protein and formation of inclusion body because removal of mitochondrial targeting signal (MTS) by peptidase in mitochondria after import of mitochondrial proteins into matrix is necessary for correct folding of the protein into mature structure and bacteria do not have such machinery (Chacinska et al., Cell 138: 628, 2009). We have previously tried to purify His-tagged full-length human COQ5 protein expressed in *E. coli*, but it formed inclusion under all conditions commonly employed. We could only purify that recombinant protein under denaturing condition with 8 M urea, but protein precipitated severely once urea was removed by buffer exchange with phosphate-buffer saline (PBS). Nevertheless, one publication has compared and indicated that removal of N-terminal MTS of mouse endonuclease G, a mitochondrial matrix protein, could increase the solubility of the protein when its mutant was expressed in *E. coli* although no data were shown for the comparison (Yoon et al., Acta. Crystallogr. Sect. F. Struct Biol. Cryst Commun 65: 504, 2009).

So far, other than Baba's article on yeast COQ5 (Baba et al., J Biol Chem 279: 10052, 2004), no publication has reported the purification of COQ5 protein for generation of antibody. Although they indeed expressed mature form of recombinant yeast COQ5 protein without N-terminal NITS in *E. coli*, denaturing conditions with the use of urea followed by SDS-PAGE purification were still applied for purification of recombinant yeast COQ5 proteins. The antibody produced by this group against such denatured COQ5 protein was not affinity-purified either (Baba et al., J Biol Chem 279: 10052, 2004). These results indicated that additional strategy might be needed to purify yeast COQ5 protein as soluble protein. Because yeast COQ5 protein is not a soluble matrix protein but is associated with other protein on mitochondrial inner membrane as an insoluble complex (Baba et al., J Biol Chem 279: 10052, 2004), we suspected that even if MTS-truncated could be expressed as native form in the cytoplasm of *E. coli*, it might become associated with plasma membrane of bacteria to form insoluble complex. The rationale is that mitochondria in modern eukaryotes is from ancient bacteria during evolution and so biochemical characteristics of mitochondrial proteins in mitochondrial matrix and inner membrane are often similar to that in cytoplasm and plasma membrane of bacteria, respectively (Pallen, Trends Microbiol 19: 58, 2011).

The earliest commercial antibodies for human COQ5 available were from Abgent (Cat.#: AP9319c) and Protein-Tech (Cat.#: 17453-1-AP), although more commercial antibodies came out in 2012 with similar description as that in datasheets of these two antibodies. By using information from online datasheets of these two antibodies from Abgent and ProteinTech as examples, we could find many problems for those commercial antibodies. For example, they did not prove the detection of endogenous human COQ5 protein by these antibodies, but just used mouse tissues as demonstration. No validation experiments, such as overexpression or knockdown of COQ5 gene in cells, were performed to confirm the specificity either. Moreover, the size of protein detected by Western blot by antibodies from different sources was not the same. On the other hand, the antigen of Protein-Tech's antibody, as His-tagged full-length human COQ5 protein containing MTS, is also a commercial product (Cat. #: ag10203). Although no description about the purification condition could be found on the datasheet of the antigen, it appears that this purified recombinant protein is not soluble in aqueous solution without ionic detergent as the protein is resolved in PBS containing the detergent Sarcosyl (N-lauryl-sarcosine) at the concentration of 0.7%.

SUMMARY OF THE INVENTION

This invention is based on the discovery that treating bacteria cell lysate with low concentration of an ionic detergent, such as SDS, might assist the dissociation of MTS-truncated human COQ5 protein from bacteria membrane in addition to lysing bacteria with lysozyme and deoxyribonuclease I (DNase I). By doing this way, the purified MTS-truncated human COQ5 protein could remain in soluble form without any aggregation and precipitation at 4° C. for several days or after being stored at −20° C. for several months.

Thus, in one aspect, the present invention provides a producing and purifying method of soluble recombinant. COQ5 protein under native conditions. The method of the invention comprises steps of: providing an E. coli host cell transformed with an expression vector containing DNA fragments that encode sequence for soluble COQ5 protein; inducing the expressing of recombinant soluble COQ5 protein in the E. coli host cell; lysing the bacterial cells by a lysis buffer comprising lysozyme and DNase I; treating the cell lysate with low concentration of ionic detergent; centrifugation for removing insoluble proteins or debris and collecting supernatant containing the recombinant soluble COQ5 protein; and applying the supernatant to Ni-NTA heads under native condition (without using urea or any other detergents) to purify the recombinant soluble COQ5 protein.

In certain embodiments of this invention, the said soluble COQ5 protein is a mitochondrial targeting signal (MTS)-truncated human COQ5 protein. In other embodiments of this invention, the said soluble COQ5 protein is a MTS-truncated human COQ5 protein with His tag at N-terminus, comprising the amino acid sequence of SEQ ID NO.2.

In certain embodiments of this invention, the said E. coli host cell is induced to express recombinant protein at a temperature in the range of 10-24° C. In other embodiments of this invention, the said E. coli host cell is induced to express recombinant protein at 16° C.

In certain embodiments of this invention, the low concentration of ionic detergent comprises no more than 0.3% of sodium dodecyl sulfate (SDS). In other embodiments of this invention, the final concentration of SDS in the lysate solution is 0.05% to 0.1%.

In another aspect of the invention, it relates to a recombinant soluble COQ5 protein produced by the method of this invention. In certain embodiments of this invention, the said soluble COQ5 protein is a MTS-truncated human COQ5 protein. The recombinant soluble COQ5 protein obtained according to the producing and purifying method described above does not become aggregated or form precipitation once solution during purification is exchanged with PBS buffer and the protein is concentrated, which may improve protein yield available for antibody production and subsequent affinity purification of anti-COQ5 antibodies.

Other features or advantages of the present invention will be apparent from the following drawings and detailed description of several embodiments, and also from the appending claims.

DETAILED DESCRIPTION OF THE INVENTION

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE

Example 1

Production and Purification of Soluble Recombinant Human COQ5 Protein

Construction of Vector for Expressing MTS-Truncated Human COQ5 Protein

Accession number for reference sequence human COQ5 gene and COQ5 protein is NM_032314 and NP_115690, respectively, from GenBank in National Center for Biotechnology Information (NCBI). Because the exact length of MTS for human COQ5 protein has not been reported, the length of N-terminal MTS for human COQ5 protein was predicted by using the reference protein sequence of COQ5 protein and three online tools: Target P (www.cbs.dtu.dk/services/TargetP/), MitoProt II (ihg.gsf.de/ihg/mitoprot.html) and UniprotKB (www.uniprot.org/uniprot/). However, due to different algorithms used by different programs, the results of prediction from three online tools are often different and may not match with real MTS occurred in cells. Predicted lengths of MTS for human COQ5 protein were 17, 42, and 49 amino acids in length from three different online tools. The longest length of MTS predicted by UniprotKB was chosen for the construction of expression plasmid.

DNA segment of the open reading frame (ORF) of human COQ5 gene, +148 to +984 nt, without the first 147 nt encoding MTS was generated by PCR by using cDNA from human 143B cell line as the template with the forward primer NdeI-hCOQ5: 5'-GGGAATTC CATATGGCGGAAACGCACTTTGGG-3'; SEQ ID NO: 3; and reverse primer hCOQ5-XhoI-R: (5'-GACCG CTCGAGTTAAAGTTTGAAGCCAGAATG-3'); SEQ ID NO: 4. The NdeI-hCOQ5 primer contained an NdeI restriction site (underlined sequence) followed by +148 to +165 of COQ5 ORF. The hCOQS-XhoI-R primer contained an XhoI restriction site (underlined sequence) followed by +984 to +964 of COQ5 ORF containing the stop codon. The size of amplicon from these two primers was 862 bp. PCR product was digested with NdeI and XhoI and ligated into pET-15b vector (Novagen) to generate pET15b-ΔMTS-hCOQ plasmid to express recombinant MTS-truncated human COQ5 protein with N-terminal His-tag (His-ΔMTS-hCOQS) in *E. coli* (BL21) DE3. The DNA sequence of the cloned insert was confirmed to be the same as that of the reference sequence by direct sequencing. The total length of the recombinant protein expressed by the pET15b-ΔMTS-hCOQ5 plasmid was 299 amino acids because it contained not only the 278 amino acids (without the MTS from the full-length protein in 327 amino acids), but also other 21 amino acids on the pET15b vector for initiation of translation (Met), His-tag, thrombin cleavage site, NdeI cloning site, and other connecting amino acids on the N-terminus. The molecular weight of this recombinant protein was predicted to be 34 kD based on the results from the analysis on ProtParam (web.expasy.org/protparam/).

Expression and Purification of MTS-Truncated Human COQ5 Protein

Expression of His-ΔMTS-hCOQ5 protein in *E. coli* (BL21) DES was induced by 0.5 mM isopropyl-β-D-thiogalactopyranoside (IPTG) at 16° C. for 8-16 hour. Bacterial culture in 2 L were centrifuged at 6000×g at 4° C. and then bacteria pellet was lysed by lysis buffer containing 20 mM Tris-Cl buffer (pH 8.0) containing 150 mM NaCl, 0.5 mg/mL lysozyme, and 5 µg/mL DNase I at 4° C. for 1 hour. Then SDS stock solution was added into the lysis buffer to a final concentration of 0.1%, and then protein was incubated at 4° C. for another 8 hours on shaker. To remove insoluble proteins or cell debris, the solution containing protein extract was centrifuged at 10,000×g at 4° C.

Next, soluble His-ΔMTS-hCOQ5 protein in supernatant was purified by nickel-nitrilotriacetic acid (Ni-NTA) agarose (Qiagen) under native condition modified from the protocols in Qiagen's online handbook, entitled "THE QIAEXPRESSIONIST" (fifth edition) downloaded from www.qiagen.com/HB/QIAexpressionist. In brief, supernatant from lysate was incubated with Ni-NTA and put into a column followed by passing through a gradient of imidazole: 10 mM, 20 mM, 50 mM, 100 mM, and 300 mM in 20 mM Tris-Cl buffer (pH 8.0) containing 150 mM NaCl and protease inhibitor cocktail (BioShop). SDS-PAGE staining with Coomassie brilliant blue was performed to check purity and quantity of purified proteins in each fraction. The presence of His-tag protein was confirmed by Western blot analysis using mouse anti-His antibody (GE) as the primary antibody and horseradish peroxidase-conjugated goat anti-mouse IgG as the secondary antibody. The purified protein was also confirmed to be human COQ5 protein by the analysis on matrix-assisted laser desorption/ionization-time of flight (MALDI-TOF) mass spectrometry.

On the other hand, for the comparison, the same vector containing full-length OFR of human COQ5 for expression of His-tagged full-length His-hCOQ5 (pET15b-hCOQ5) was constructed and the recombinant protein was purified by Ni-NTA beads under denaturing condition because it was still present as inclusion body when the same lysis conditions and purification steps under native condition were applied. To obtain purified His-hCOQ5 under denaturing condition, bacterial pellet was lysed by lysis buffer, which consisted of 20 mM Tris-Cl buffer (pH 8.0), 150 mM NaCl, and 8M urea, at 4° C. for 12 hr followed by the same purification procedures as for native condition except the addition of 8 M urea in all washing and elution solutions.

Figure 1:
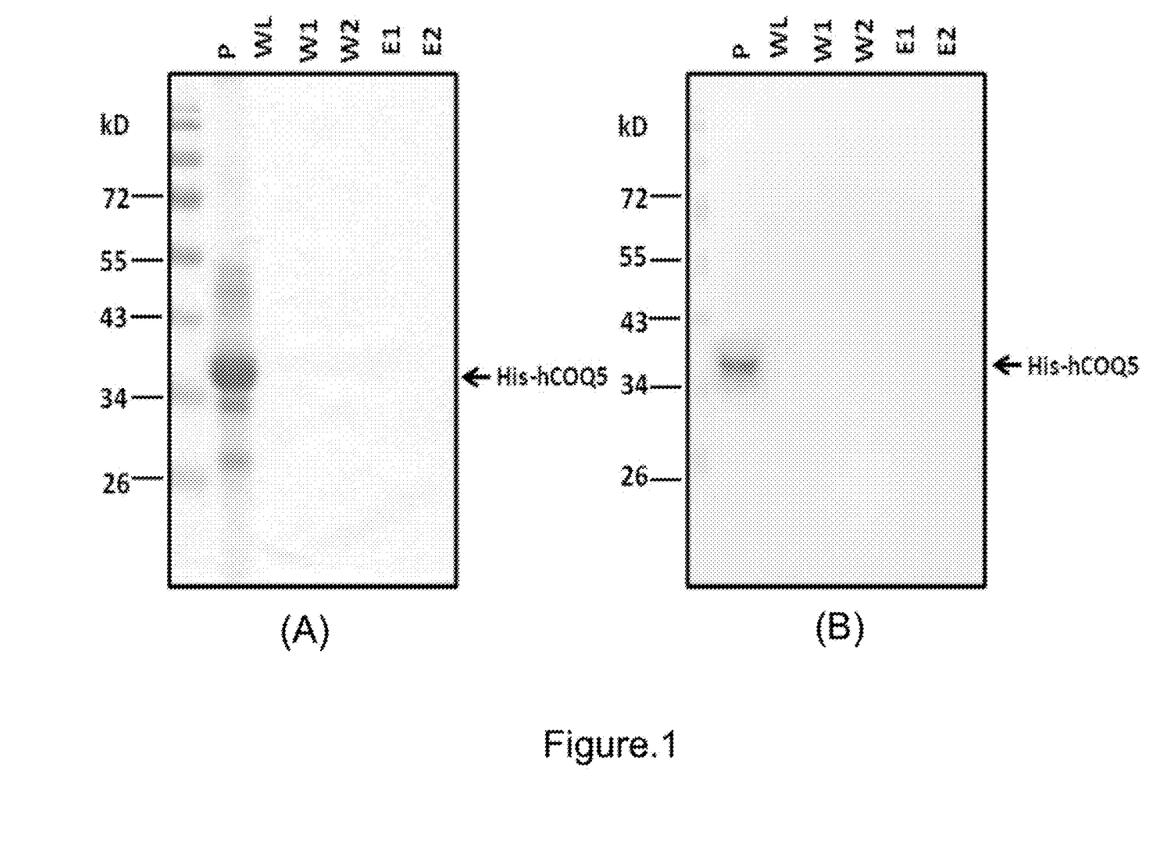
FIG. 1 shows the recovery of recombinant full-length human COQ5 protein (His-hCOQ5) during purification under native condition MTS-truncated human COQ5 protein determined by SDS-PAGE (A) and Western blot analysis with anti-His antibody (B). The predicted size of His-hCOQ5 fusion protein is 39.4 kD. Protein on Ni-NTA beads were washed (WL, W1, and W2) and eluted (E1 and E2) by 20 mM Tris-Cl buffer (pH 8.0) containing different concentrations of imidazole. P: pellet collected after centrifugation of bacterial lysate, WL: 10 mM imidazole, W1: 20 mM imidazole, W2: 50 mM imidazole, E1: 100 mM imidazole, E2: 300 mM imidazole. Results indicate that His-hCOQ5 formed inclusion body when purified under native condition as it could only found in pellet from bacterial lysate.
Figure 2:
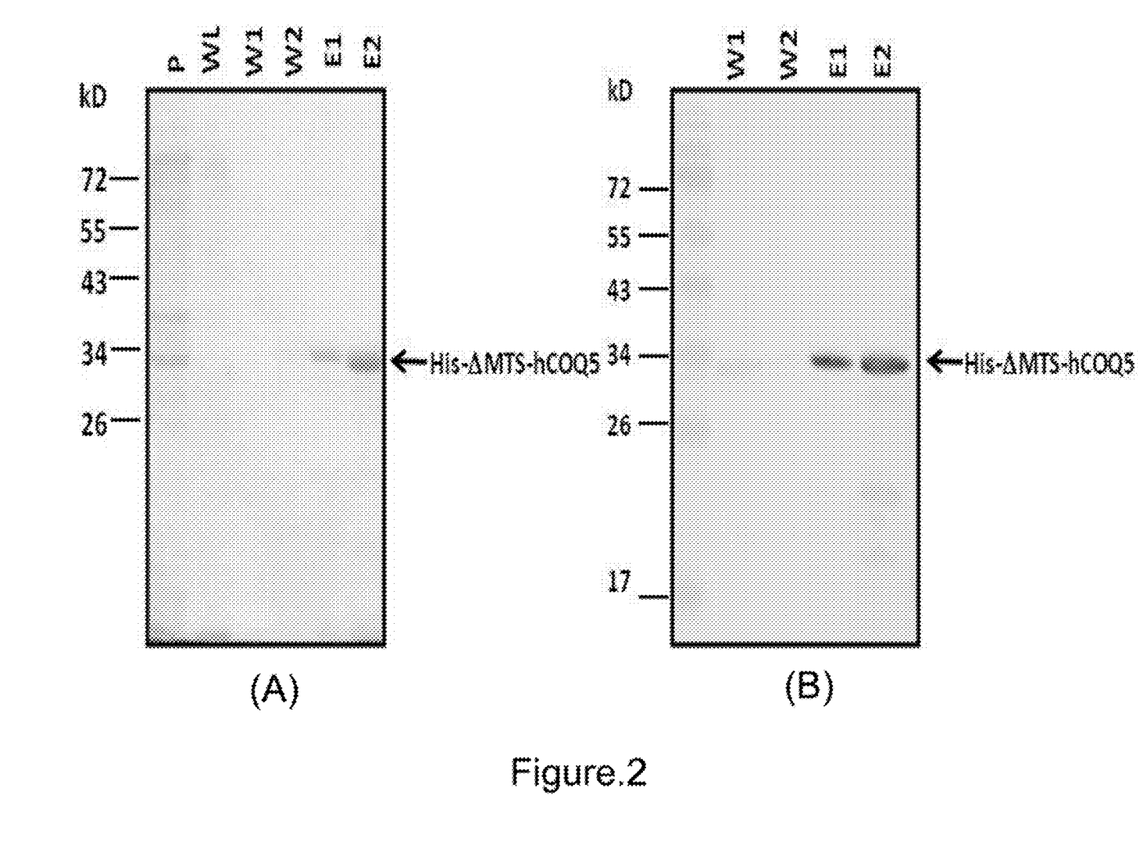
FIG. 2 shows the recovery of recombinant MTS-truncated human COQ5 protein (His-ΔMTS-hCOQ5) during the purification process under native condition determined by SDS-PAGE (A) and Western blot analysis using anti-His antibody (B). The predicted size of His-ΔMTS-hCOQ5 fusion protein is 34 kD. Protein on Ni-NTA heads were washed (WL, W1, and W2) and eluted (E1 and E2) by 20 mM Tris-Cl buffer (pH 8.0) containing different concentrations of imidazole. P: pellet collected after centrifugation of bacterial lysate, WL: 10 mM imidazole, W1: 20 nM imidazole. W2: 50 mM imidazole, E1: 100 in M imidazole, E2: 300 mM imidazole. The His-ΔMTS-hCOQ5 protein was mostly present in the fraction from two eluting solutions from supernatant of bacterial lysate.

FIGS. 1 and 2 show the purification of recombinant full-length human COQ5 protein (His-hCOQ5) and recombinant ΔMTS-human COQ5 protein (His-ΔMTS-hCOQ5) under native condition determined by SDS-PAGE and Western blot analysis, respectively. As shown in FIG. 1, recombinant full-length human COQ5 protein could not be purified under native conditions, even thought bacteria were grown at 16° C. for protein induction and its lysate was pretreated with lysis buffer containing 0.1% SDS. However, recombinant MTS-truncated human COQ5 protein could be purified under native conditions when expression was induced at 16☐ and when bacteria were treated by lysis buffer containing 0.1% SDS before purification (FIG. 2).

Example 2

Production of Rabbit Polyclonal Antibodies Against Human COQ5 (hCOQ5) Protein by Using the Purified Recombinant ΔMTS-hCOQ5 Protein Concentration and Removal of Imidazole in Purified His-ΔMTS-hCOQ5 Protein by a Centrifugal Concentrator Before antibody production, purified His-ΔMTS-hCOQ5 protein was further processed by using VIVASPIN 6 Ultrafiltration Device with 3000 molecular weight cut off (MWCO) (GE) to concentrate and filter protein and to remove imidazole. Fractions from elution of Ni-NTA beads containing purified His-ΔMTS-hCOQ5 protein were pooled and concentrated to 2 mL by centrifugation at 3000×g at 4° C. for 10 minutes. The concentrated protein solution (2 ml) in concentrator body was mixed with 2 mL of phosphate-buffered saline (PBS) containing protease inhibitor (PI) to reduce concentration of imidazole and then was centrifuged again to the volume of 2-3 ml solution in concentrator body. This buffer exchange step was repeated for another four times. The final protein solution was then sent to GeneTex Corporation (Taiwan) to generate rabbit polyclonal antibody and the subsequent affinity purification of antibody. The amount of purified recombinant His-ΔMTS-hCOQ5 protein needed for immunization of rabbits and affinity purification was 2 mg and 1 mg, respectively. His-ΔMTS-hCOQ5 remained in clear and soluble from without obvious change in protein concentration for several days at 4° C. or after thawing the protein solution frozen at −20° C. for about 2 months between the time of rabbit immunization and affinity-purification of antiserum, indicating the long-term stability of purified His-ΔMTS-hCOQ5 protein.

Comparison on the Degree of Protein Aggregation and Protein Yield for His-hCOQ5 Purified Under Denaturing Condition and His-ΔMTS-hCOQ5 Protein Purified Under Native Condition Following Buffer Exchange with PBS After protein was concentrated by using VIVASPIN 6 Ultrafiltration Device (GE) about 2 ml, protein concentration of concentrated protein was first determined by measuring absorbance at 280 nm. The protein recovery up to this step was calculated to be 10.2 mg and 25.3 mg for His-hCOQ5 and His-ΔMTS-hCOQ5, respectively. A fraction of concentrated protein with the same volume and same absorbance for two proteins was taken for further buffer exchange for comparison. For each buffer exchange with PBS, 1 mL of concentrated protein was mixed gently with 333 μL of PBS followed by centrifugation to about 1 ml. The same steps were repeated for another four times. The amount of PBS was less here to ensure gradual removal of urea for His-hCOQ5.

Figure 3:
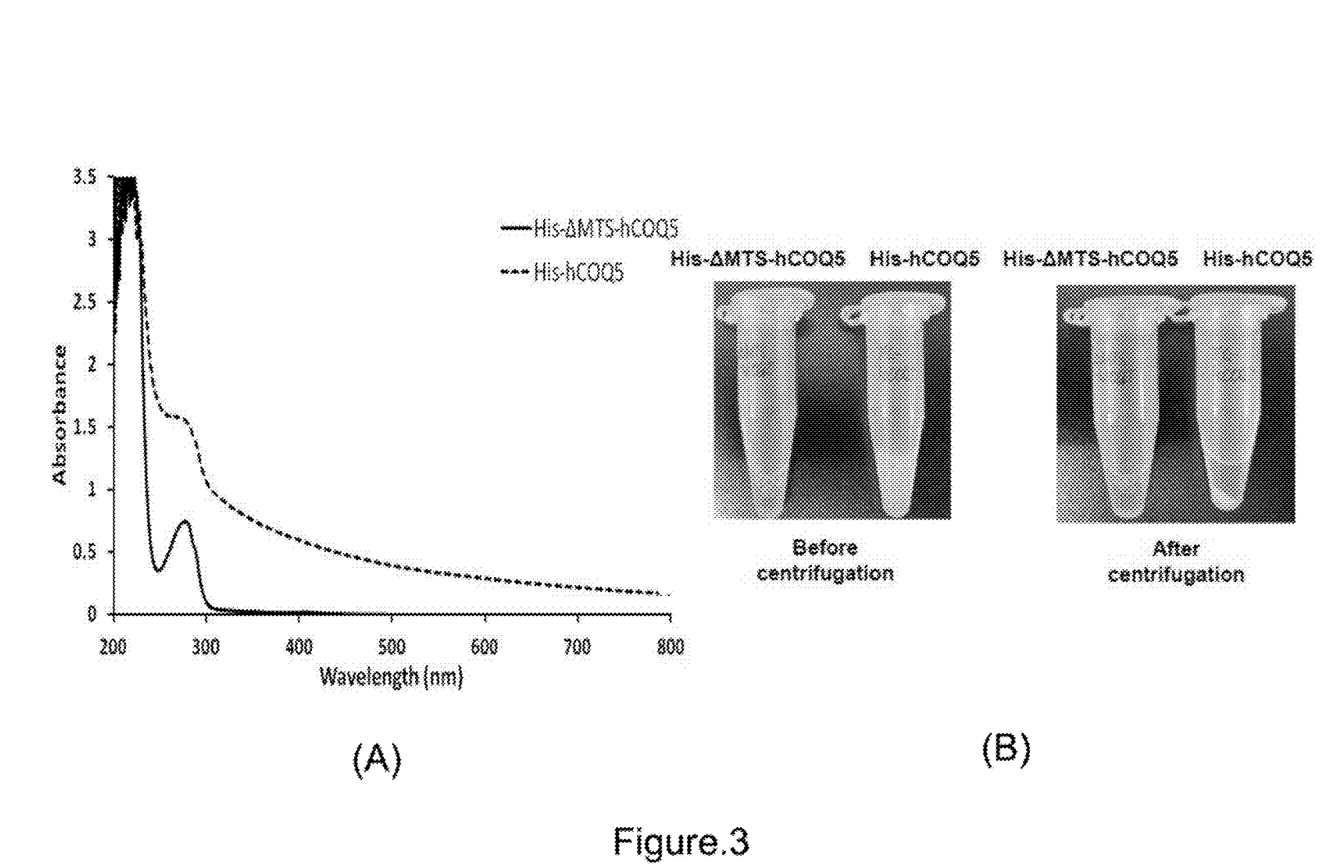
FIG. 3 demonstrates formation of aggregation and precipitation in His-hCOQ5 protein solution, but not His-ΔMTS-hCOQ5 protein solution after buffer exchange of protein solutions with PBS by a centrifugal concentrator. (A) Results of wavelength scan showing the absorbance (y-axis) to wavelength (x-axis) relationship of two protein solutions after 10-fold dilution with PBS were used to demonstrate the presence of aggregation in His-hCOQ5 solution after forth buffer exchange with PBS. Dashed line and solid line indicated the spectrums for His-hCOQ5 and His-ΔMTS-hCOQ5, respectively. (B) High degree of protein precipitation after fifth buffer exchange could be easily visualized. Left and right photographs showed the appearance of two protein solutions in microcentrifuge tubes before and after centrifugation at 12000×g at 4'C for 5 min. respectively.

Right after four times of buffer exchange was completed, the His-hCOQ5 protein solution purified under denaturing condition exhibited high turbidity, but the His-ΔMTS-hCOQ5 protein solution purified under native condition remained in clear form. The results of wavelength scan between 200 nm to 800 nm for these two protein solutions with 10-fold dilution in PBS was performed to demonstrate the presence of insoluble protein aggregate, which could scatter light at all wavelengths, in His-hCOQ5 protein solution, but not His-ΔMTS-hCOQ5 protein, could be observed (FIG. 3A). The marked turbidity and precipitation persisted in His-hCOQ5 protein solution after the fifth buffer exchange was completed. After centrifugation at a high speed (12000×g), there was a large pellet in the tube with His-hCOQ5 protein, but not His-ΔMTS-hCOQ5. The difference between two protein solutions before centrifugation and after centrifugation could easily be visualized (FIG. 3B). The absorbance of supernatant at 280 nm for His-hCOQ5 solution and His-ΔMTS-hCOQ5 with 10-fold dilution was 0.1207 and 0.6214, respectively. Therefore, starting from 2 L of bacterial culture, the yield of purified His-hCOQ5 and His-ΔMTS-hCOQ5 protein recovered after 5 times of buffer exchange was 1.5 mg and 17.6 mg, respectively. Therefore, it was much easier and cheaper to use soluble His-ΔMTS-hCOQ5 as the immunogen for production of anti-hCOQ5 antibody and further purification of antibody by affinity columns.

Figure 4:
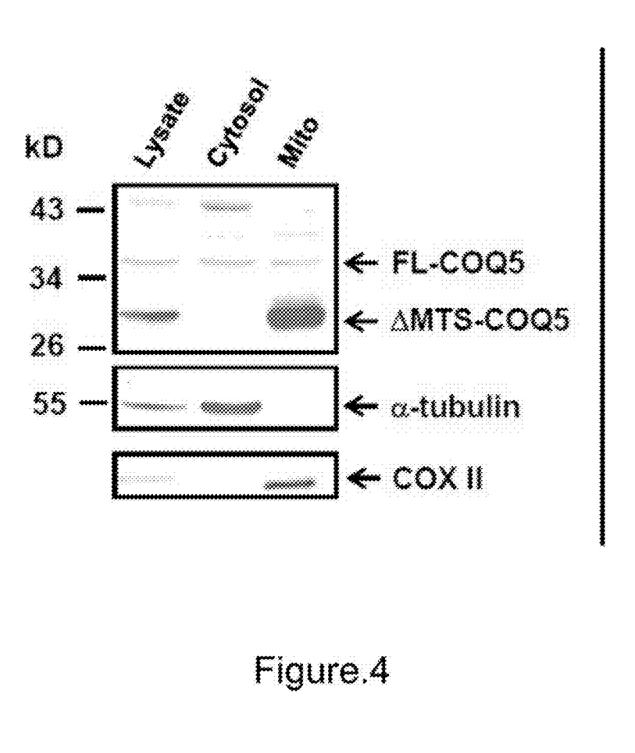
FIG. 4 shows the detection of human COQ5 protein in total lysate, cytosol, and mitochondria of 143B cells by Western blot with the anti-COQ5 antibody. COX II, mtDNA-encoded protein, and α-tubulin, cytosolic cytoskeleton protein, are markers to ensure the lack of cytosolic protein in mitochondria and the absence of mitochondrial protein in the cytosolic fraction, respectively.

Detection of Human COQ5 Protein in Human 143B Cells by Western Blot with the Anti-COQ5 Antibody The ability of this antibody to detect full-length and predicted mature fort of endogenous human COQ5 protein was further examined by Western blot analysis by using cell lysate, cytosolic fraction, and mitochondrial fraction from human 143B cell line. Results of Western blot shown in FIG. 4 showed that both the full-length form (37.1 kD) and predicted mature form (31.8 kD), which was the major form of endogenous COQ5 protein in human cells, could be detected in cell lysate by polyclonal antibody produced with the purified recombinant ΔMTS-hCOQ5 protein. Full-length COQ5 protein (FL-COQ5) could be detected in both cytosolic and mitochondrial fraction (Mito) and the levels were not very different among total lysate, cytosol, and mitochondria. Mature form of human COQ5 (ΔMTS-COQ5) could be detected in the mitochondria, but not in the cytosol, and the level was enriched in the mitochondria compared with that of total lysate (FIG. 4).

To further prove that the two protein bands with molecular weight of 37.1 kD and 31.8 kD detected by the affinity-purified antibody in FIG. 4 was indeed full-length human COQ5 protein and mature COQ5 protein, respectively, the strategies of overexpression and knockdown of COQ5 gene were employed.

Figure 5:
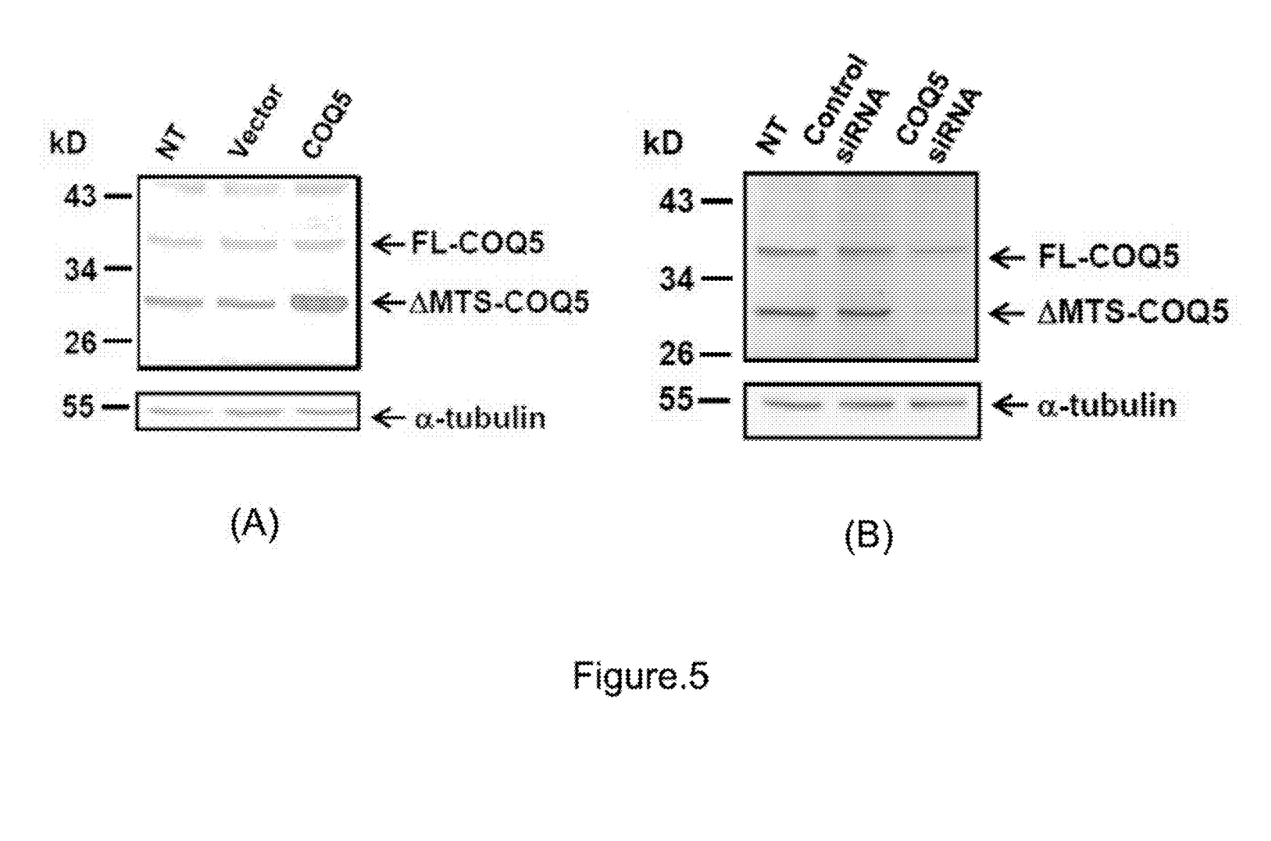
FIG. 5 shows the verification on the specificity of anti-COQ5 antibody on recognizing full-length and mature form of human COQ5 protein in 143B cells by Western blot following transient overexpression (A) and knockdown of COQ5 gene (B). Detection of α-tubulin was performed as a loading control. The predicted molecular weight of full-length COQ5 protein (FL-COQ5) and mature COQ5 without MTS (ΔMTS-COQ5) was 37.1 and 31.8 kD, respectively.

As shown by FIG. 5A, in the experiment of transient overexpression of COQ5 gene by transient transfection of a plasmid expressing COQ5 gene for 72 hr, the transfection of vector alone (Vector) did not affect COQ5 levels compared with that of non-transfected cells (NT). However, the sample transfected with COQ5 gene (COQ5) had markedly higher levels of ΔMTS-COQ5 (increased intensity of signal for the 31.8-kD band), but not that of FL-COQ5 (the 37.1-kD band), in 143B cells, proving the identity of the 31.8-kD band. Next, we knocked down expression of COQ5 gene by transiently transfection of small-interfering RNA (siRNA) for human COQ5 gene into 143B cells. FIG. 5B shows that in the experiment for transient knockdown of COQ5 gene for 72 hr, transfection with negative-control siRNA did not affect levels of COQ5 protein compared with NT sample. However, transfection with COQ5 siRNA dramatically decrease levels of both ΔMTS-COQ5 (31.8-kD protein band) and FL-COQ5 (37.1-kD protein hand) as detected by the antibody. The degree of decrease in full-length form (42.6% reduction) was less than that for mature form (89.9% reduction). Based on the results of experiments shown in FIG. 5, the antibody produced against the soluble recombinant human COQ5 protein was demonstrated to be specific for both precursor and mature form of human COQ5 protein.

OTHER EMBODIMENTS

All of the features disclosed in this specification may be combined in any combination. Each feature disclosed in this specification may be replaced by an alternative feature serving the same, equivalent or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of producing and purifying recombinant mitochondrial targeting signal (MTS)-truncated coenzyme Q5 homolog (COQ5) protein in non-denaturing conditions, comprising the steps of:
   providing an *Escherichia coli* (*E. coli*) host cell transformed with an expression vector containing a DNA fragment that encodes the recombinant COQ5 protein;
   inducing the expression of the recombinant COQ5 protein in the *E. coli* host cell;
   lysing the bacterial cells with a lysis buffer comprising lysozyme and deoxyribonuclease I (DNase I);
   pre-treating the bacterial cell lysate with less than 0.2% of an ionic detergent;
   centrifuging the cell lysate for removing insoluble proteins or debris and collecting the supernatant containing the recombinant COQ5 protein; and
   applying the supernatant to nickel-nitrilotriacetic acid (Ni-NTA) beads under native conditions that lack exposure to urea to obtain purified recombinant COQ5 protein.

2. The method of claim 1, wherein the recombinant COQ5 protein is a human COQ5 protein without a mitochondrial targeting signal (MTS).

3. The method of claim 1, wherein the *E. coli* host cell is induced to express recombinant COQ5 protein at a temperature of 10-24° C.

4. The method of claim 3, wherein the *E. coli* host cell is induced to express recombinant COQ5 protein at 16° C.

5. The method of claim 1, wherein the ionic detergent is sodium dodecyl sulfate (SDS).

6. The method of claim 5, wherein the final concentration of SDS added in the lysate solution is 0.05% to 0.1%.

7. A method of producing and purifying recombinant mitochondrial targeting signal (MTS)-truncated coenzyme Q5 homolog (COQ5) protein in non-denaturing conditions, comprising the steps of:
   providing an *Escherichia coli* (*E. coli*) host cell transformed with an expression vector containing a DNA fragment that encodes the recombinant COQ5 protein;
   inducing the expression of the recombinant COQ5 protein in the *E. coli* host cell;
   lysing the bacterial cells with a lysis buffer comprising lysozyme and deoxyribonuclease I (DNase I);
   pre-treating the bacterial cell lysate with less than 0.2% of an ionic detergent;
   centrifuging the cell lysate for removing insoluble proteins or debris and collecting the supernatant containing the recombinant COQ5 protein; and
   applying the supernatant to nickel-nitrilotriacetic acid (Ni-NTA) beads under native conditions that lack exposure to urea to obtain purified recombinant COQ5 protein, wherein the recombinant COQ5 protein is a MTS-truncated human COQ5 protein with 6× histidine tag (His tag) at the N-terminus, comprising the amino acid sequence of SEQ ID NO: 2.

\* \* \* \* \*

```
                         SEQUENCE LISTING

<160> NUMBER OF SEQ ID NOS: 4

<210> SEQ ID NO 1
<211> LENGTH: 327
<212> TYPE: PRT
<213> ORGANISM: Homo Sapiens

<400> SEQUENCE: 1

Met Ala Ala Pro Gly Ser Cys Ala Leu Trp Ser Tyr Cys Gly Arg Gly
1               5                   10                  15

Trp Ser Arg Ala Met Arg Gly Cys Gln Leu Leu Gly Leu Arg Ser Ser
            20                  25                  30

Trp Pro Gly Asp Leu Leu Ser Ala Arg Leu Leu Ser Gln Glu Lys Arg
        35                  40                  45

Ala Ala Glu Thr His Phe Gly Phe Glu Thr Val Ser Glu Glu Lys
    50                  55                  60

Gly Gly Lys Val Tyr Gln Val Phe Glu Ser Val Ala Lys Lys Tyr Asp
65                  70                  75                  80

Val Met Asn Asp Met Met Ser Leu Gly Ile His Arg Val Trp Lys Asp
                85                  90                  95

Leu Leu Leu Trp Lys Met His Pro Leu Pro Gly Thr Gln Leu Leu Asp
            100                 105                 110

Val Ala Gly Gly Thr Gly Asp Ile Ala Phe Arg Phe Leu Asn Tyr Val
        115                 120                 125

Gln Ser Gln His Gln Arg Lys Gln Lys Arg Gln Leu Arg Ala Gln Gln
130                 135                 140

Asn Leu Ser Trp Glu Glu Ile Ala Lys Glu Tyr Gln Asn Glu Glu Asp
145                 150                 155                 160

Ser Leu Gly Gly Ser Arg Val Val Val Cys Asp Ile Asn Lys Glu Met
                165                 170                 175

Leu Lys Val Gly Lys Gln Lys Ala Leu Ala Gln Gly Tyr Arg Ala Gly
            180                 185                 190

Leu Ala Trp Val Leu Gly Asp Ala Glu Glu Leu Pro Phe Asp Asp Asp
        195                 200                 205

Lys Phe Asp Ile Tyr Thr Ile Ala Phe Gly Ile Arg Asn Val Thr His
    210                 215                 220

Ile Asp Gln Ala Leu Gln Glu Ala His Arg Val Leu Lys Pro Gly Gly
225                 230                 235                 240

Arg Phe Leu Cys Leu Glu Phe Ser Gln Val Asn Asn Pro Leu Ile Ser
                245                 250                 255

Arg Leu Tyr Asp Leu Tyr Ser Phe Gln Val Ile Pro Val Leu Gly Glu
            260                 265                 270

Val Ile Ala Gly Asp Trp Lys Ser Tyr Gln Tyr Leu Val Glu Ser Ile
        275                 280                 285

Arg Arg Phe Pro Ser Gln Glu Glu Phe Lys Asp Met Ile Glu Asp Ala
    290                 295                 300

Gly Phe His Lys Val Thr Tyr Glu Ser Leu Thr Ser Gly Ile Val Ala
305                 310                 315                 320

Ile His Ser Gly Phe Lys Leu
                325
```

```
<210> SEQ ID NO 2
<211> LENGTH: 299
<212> TYPE: PRT
<213> ORGANISM: Artificial Sequence
<220> FEATURE:
<223> OTHER INFORMATION: nuclear gene encoding mitochondrial protein

<400> SEQUENCE: 2

Met Gly Ser Ser His His His His His Ser Ser Gly Leu Val Pro
1               5                   10                  15

Arg Gly Ser His Met Ala Glu Thr His Phe Gly Phe Glu Thr Val Ser
            20                  25                  30

Glu Glu Glu Lys Gly Gly Lys Val Tyr Gln Val Phe Glu Ser Val Ala
                35                  40                  45

Lys Lys Tyr Asp Val Met Asn Asp Met Met Ser Leu Gly Ile His Arg
    50                  55                  60

Val Trp Lys Asp Leu Leu Leu Trp Lys Met His Pro Leu Pro Gly Thr
65                  70                  75                  80

Gln Leu Leu Asp Val Ala Gly Gly Thr Gly Asp Ile Ala Phe Arg Phe
                85                  90                  95

Leu Asn Tyr Val Gln Ser Gln His Gln Arg Lys Gln Lys Arg Gln Leu
            100                 105                 110

Arg Ala Gln Gln Asn Leu Ser Trp Glu Glu Ile Ala Lys Glu Tyr Gln
        115                 120                 125

Asn Glu Glu Asp Ser Leu Gly Gly Ser Arg Val Val Cys Asp Ile
130                 135                 140

Asn Lys Glu Met Leu Lys Val Gly Lys Gln Lys Ala Leu Ala Gln Gly
145                 150                 155                 160

Tyr Arg Ala Gly Leu Ala Trp Val Leu Gly Asp Ala Glu Glu Leu Pro
                165                 170                 175

Phe Asp Asp Asp Lys Phe Asp Ile Tyr Thr Ile Ala Phe Gly Ile Arg
            180                 185                 190

Asn Val Thr His Ile Asp Gln Ala Leu Gln Glu Ala His Arg Val Leu
        195                 200                 205

Lys Pro Gly Gly Arg Phe Leu Cys Leu Glu Phe Ser Gln Val Asn Asn
    210                 215                 220

Pro Leu Ile Ser Arg Leu Tyr Asp Leu Tyr Ser Phe Gln Val Ile Pro
225                 230                 235                 240

Val Leu Gly Glu Val Ile Ala Gly Asp Trp Lys Ser Tyr Gln Tyr Leu
                245                 250                 255

Val Glu Ser Ile Arg Arg Phe Pro Ser Gln Glu Glu Phe Lys Asp Met
            260                 265                 270

Ile Glu Asp Ala Gly Phe His Lys Val Thr Tyr Glu Ser Leu Thr Ser
        275                 280                 285

Gly Ile Val Ala Ile His Ser Gly Phe Lys Leu
    290                 295

<210> SEQ ID NO 3
<211> LENGTH: 32
<212> TYPE: DNA
<213> ORGANISM: Artificial Sequence
<220> FEATURE:
<223> OTHER INFORMATION: NdeI-hCOQ5

<400> SEQUENCE: 3
gggaattcca tatggcggaa acgcactttg gg                              32
```

```
<210> SEQ ID NO 4
<211> LENGTH: 32
<212> TYPE: DNA
<213> ORGANISM: Artificial Sequence
<220> FEATURE:
<223> OTHER INFORMATION: hCOQ5-XhoI-R

<400> SEQUENCE: 4
gaccgctcga gttaaagttt gaagccagaa tg                                    32
```